United States Patent [19]
Foltz et al.

[11] 4,157,714
[45] Jun. 12, 1979

[54] WIRE INSERTER AND STERILE WIRE PACK

[75] Inventors: Carl L. Foltz, Holiday; Vernon H. Troutner, St. Petersburg; Arthur F. Trott, Largo, all of Fla.

[73] Assignee: Concept, Inc., Clearwater, Fla.

[21] Appl. No.: 852,030

[22] Filed: Nov. 16, 1977

Related U.S. Application Data

[63] Continuation of Ser. No. 610,869, Sep. 5, 1975, abandoned.

[51] Int. Cl.² ............................................. A61B 19/00
[52] U.S. Cl. ................................ 128/92 B; 128/305.1; 408/228
[58] Field of Search ............. 128/305.1, 92 B, 92 BA; 408/199, 228, 227; 32/48, 49

[56] References Cited
U.S. PATENT DOCUMENTS

| | | | |
|---|---|---|---|
| 777,543 | 12/1904 | Rich | 408/227 |
| 1,911,764 | 5/1933 | Martin | 128/305.1 |
| 2,587,980 | 3/1952 | Doepker | 408/228 |
| 3,109,222 | 11/1963 | Wiseman | 408/199 X |

FOREIGN PATENT DOCUMENTS

| | | | |
|---|---|---|---|
| 538218 | 3/1957 | Canada | 408/199 |
| 6821 | 2/1925 | Japan | 128/303.13 |
| 11132 | 12/1930 | Japan | 128/303.13 |
| 68531 | 3/1915 | Switzerland | 408/199 |
| 870902 | 6/1961 | United Kingdom | 408/199 |

*Primary Examiner*—Robert W. Michell
*Assistant Examiner*—Michael H. Thaler

[57] ABSTRACT

A portable surgical wire inserting instrument comprising a housing defining a handle, a drive casing and a nose piece removably mounted to said drive casing. The housing holds a source of power electrically connected to a motor both of which are enclosed within the housing. A wire holding tube mounted in the housing is provided with a chuck at one end adapted to grab and fixedly hold an inner chuck of a sterile wire pack inserted in the wire holding tube. Beveled gears connect the motor to the wire holding tube and are adapted to rotate the wire holding tube upon energization of the motor. The sterile wire pack comprises a wire body having a plurality of flats and a cutting tip edge of smaller length than the diameter of the wire. The inner chuck is mounted on the wire body and the wire and chuck are covered with a material covering.

4 Claims, 21 Drawing Figures

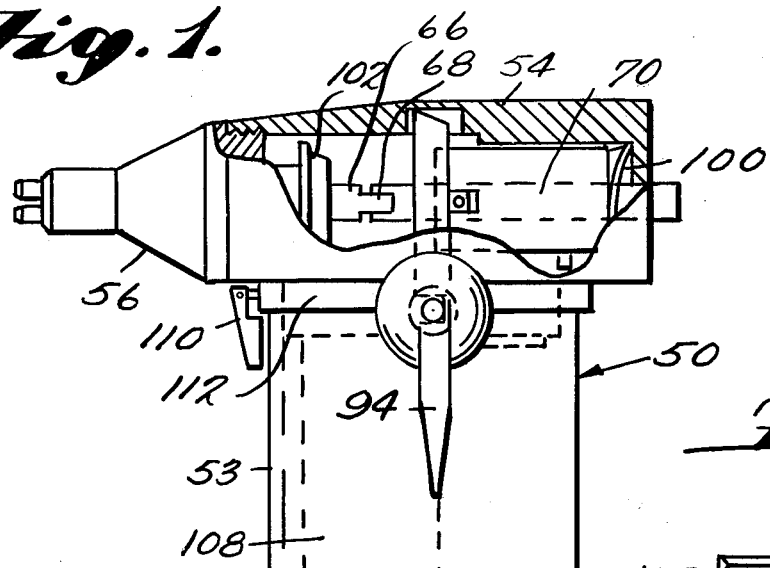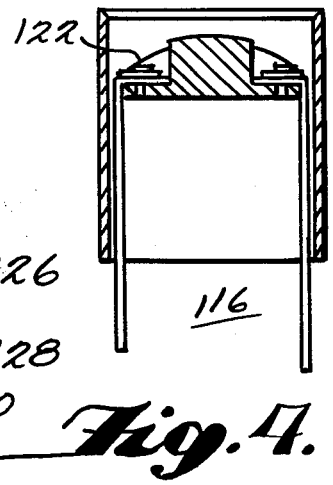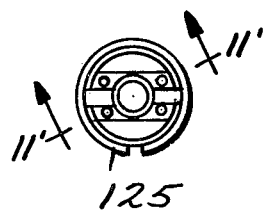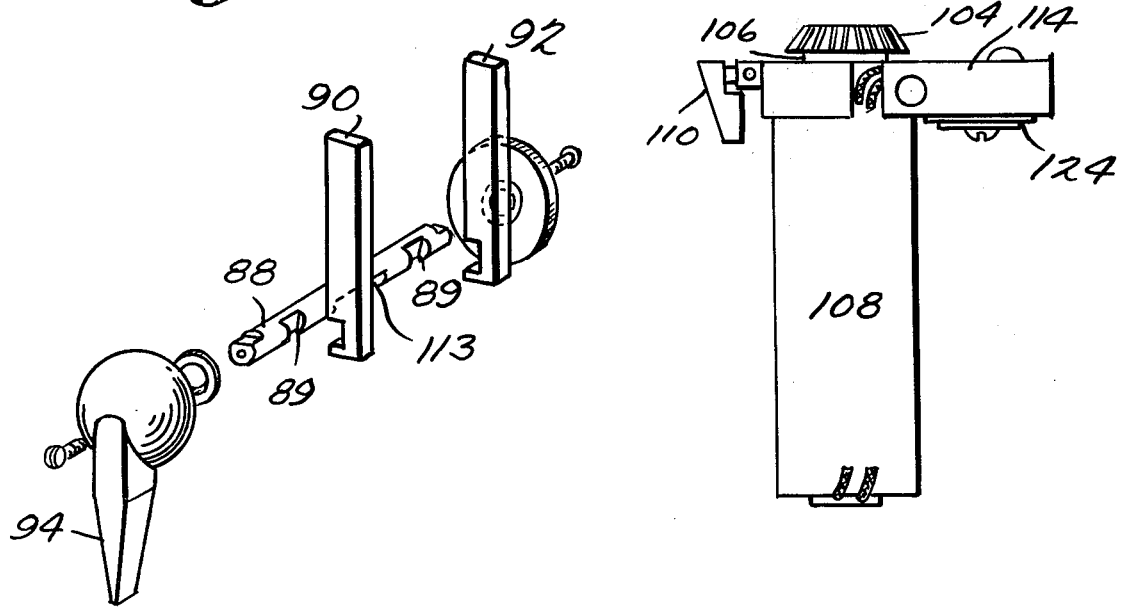

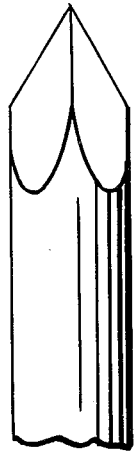
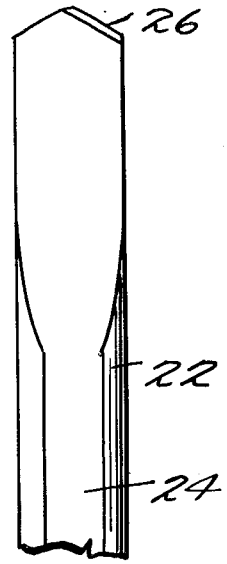
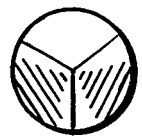
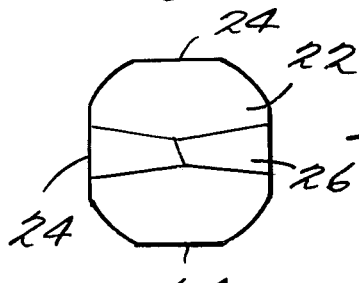
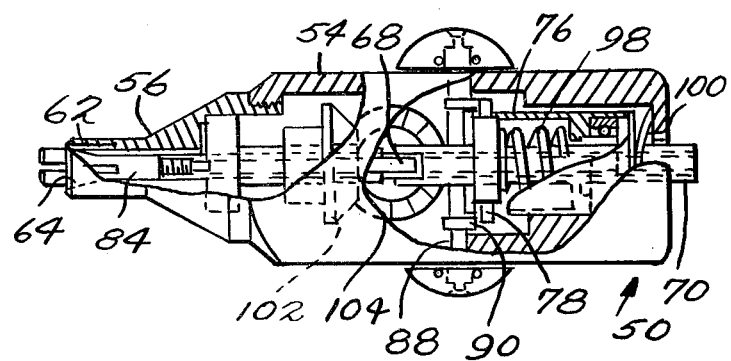

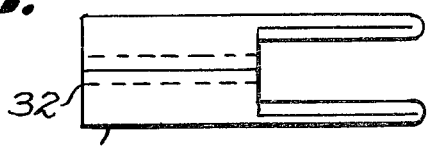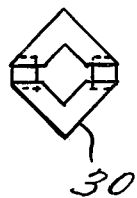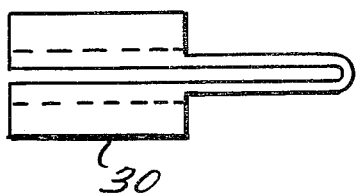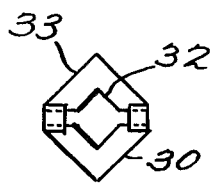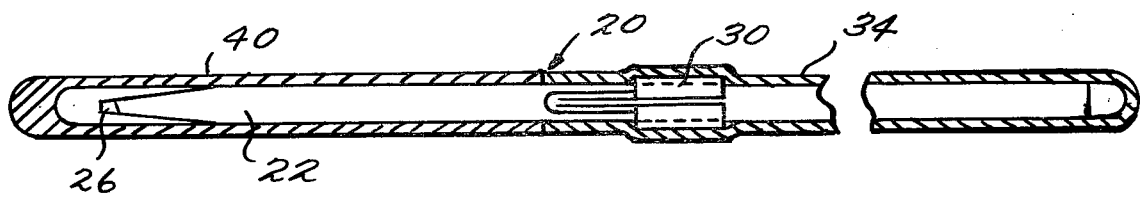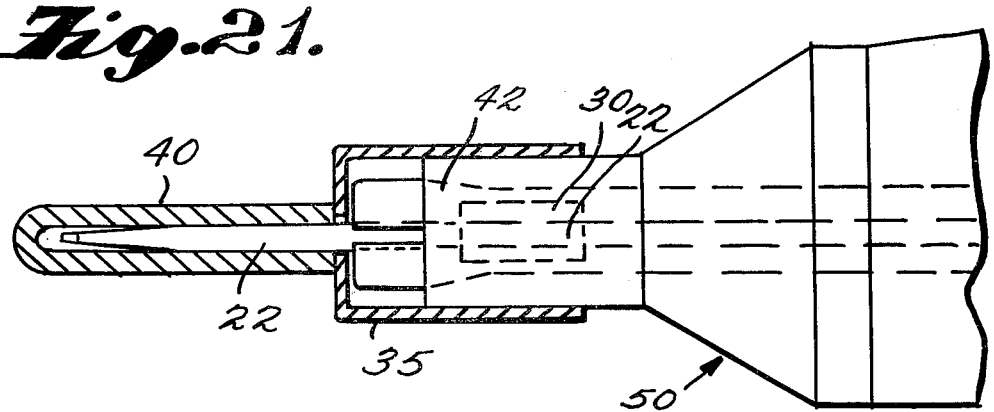

WIRE INSERTER AND STERILE WIRE PACK

This is a continuation, of application Ser. No. 610,869 filed Sept. 5, 1975 now abandoned.

BACKGROUND OF THE INVENTION

The present invention generally pertains to a surgical wire inserter adapted to insert a circular prosthetic device into or through bones to provide support and fixation while the bone structure is mending or to provide anchorage for traction but more particularly pertains to a rotary wire inserting device utilizing a sterile wire pack provided with flats to provide an anti rotational key.

In the prior art a prosthetic wire device usually 3 to 9 inches long and circular in cross section is generally inserted into the bone by means of a pre-drilled hole or more commonly by driving the wire with a suitable drill chuck and letting the wire bore its own hole by means of a spade or trocar tip. A trocar point is the point most commonly used on such wires. One such device which has been used to insert wires is a device called a Loth-Kirschner extension drill. The drill is hand operated with the drill bit being rotated by a suitable gearing which is turned by a handle much like that of a fishing reel. Another device which has been used is a pneumatic wire driver manufactured by the Stryker Corporation. This device is a hand held device with a trigger. An air supply is connected to the device by way of hoses which pass through the handle of the gun causing the wire to rotate so that it obtains a sufficient torque to be driven into the bone.

Generally speaking the prosthetic wires which are used in both of these instruments and wires which are used in the operating room are circular in cross-section ranging from 0.028 to 0.062 inches in diameter and are primarily provided with a ground spade point or a trocar point. The spade point has a cutting action by virtue of the cutting edges and consequently drills into the bone with relative ease. However, because the spade point drills a hole equal in diameter to the wire, the wire is relatively loose when it is inserted. The trocar point has more of a spreading action rather than a cutting action and therefore drills with relative difficulty which results in a tightly held wire when installed since it does not drill a clearance hole for the wire.

Because of the circular cross section and small diameter of these wires they are difficult to hold in a chuck tightly enough to prevent slipping during installation.

The present invention incorporates a wire having a tip which provides the cutting ease of the spade tip while maintaining the holding properties of the trocar tip. Futhermore, the invention provides anti rotational features on the wire which eliminate the rotational slippage of the wire in the drill chuck during installation. The novel instrument which is used to rotate the wire contains a self enclosed power unit and can be selectively adapted to rotate the wire in opposite directions. The wire inserter instrument is designed to utilize a prosthetic wire of a substantially circular cross section having one or more flats or grooves to provide anti rotational keying with the chuck which is used for installation. The wire is constructed with a spade tip specifically designed to cut a hole in the bone smaller in diameter than the major diameter of the wire so that the cutting action of the spade tip is realized while retaining a tight fit between the bone and the wire. This cutting action is achieved by restricting the cutting edges of a conventional spade point to a width less than the wire diameter. The novel wire thus achieves the desired functions of the previously described wire but is more easily gripped and installed than those prior art wires. Thus the wire combines the drilling ease of the spade point with the holding properties of the trocar point. Since the wire is more easily installed requiring less pressure and force to implant in the bone it results in an easier and more accurate installation than conventionally used wires. The material of construciton of the wire is stainless steel or other medically suitable material.

The above mentioned purposes are more readily apparent when read in conjunction with the following detailed description of the preferred embodiment of the present invention.

BRIEF DESCRIPTION OF THE DRAWINGS

FIG. 1 is a side elevational view partially in section of the drill inserter instrument;

FIG. 2 is a plan view partially in section of the drill instrument shown in FIG. 1;

FIG. 3 is an exploded enlarged view of the cam assembly of the instrument shown in FIG. 1;

FIG. 4 is a side view of the motor switch assembly removed from the instrument shown in FIG. 1;

FIG. 10 is an end plan view of the contact cap;

FIG. 11 is a cross sectional view taken along line 11'-11' of FIG. 10;

FIG. 12 is an enlarged side view of the tip of the novel prosthetic wire used in the invention;

FIG. 13 is a top plan view of the tip shown in FIG. 12;

FIG. 14 is an enlarged frontal view of the tip of the wire shown in FIG. 12;

FIG. 15 is an elevated side view and frontal view of the prior art wire tip;

FIG. 16 is a side view in section of an enlarged view of the wire capsule assembly used in the invention;

FIG. 17 is an enlarged view of the chuck shown in FIG. 16;

FIG. 18 is an enlarged top plan view of the chuck shown in FIG. 16;

FIG. 19 is a front elevational view of the chuck shown in FIG. 17;

FIG. 20 is a rear elevational view of the chuck shown in FIG. 17; and

FIG. 21 is an enlarged cross sectional view of the wire capsule assembly held in the wire inserter instrument.

DETAILED DESCRIPTION OF THE EMBODIMENT

Figure 5:
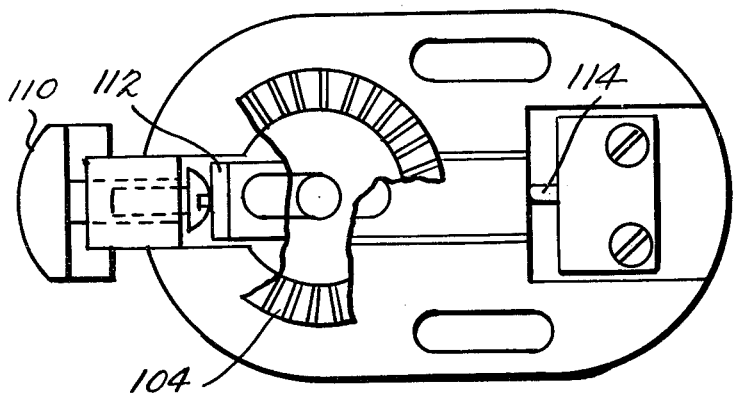
FIG. 5 is an enlarged top plan view partially in section of the motor switch assembly of FIG. 4.
Figure 8:
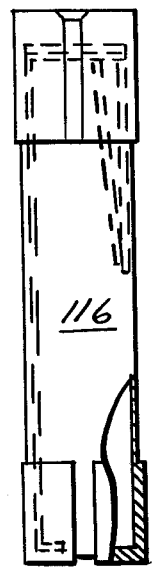
FIG. 8 is an enlarged view of the battery pack assembly of the invention.
Figure 6:
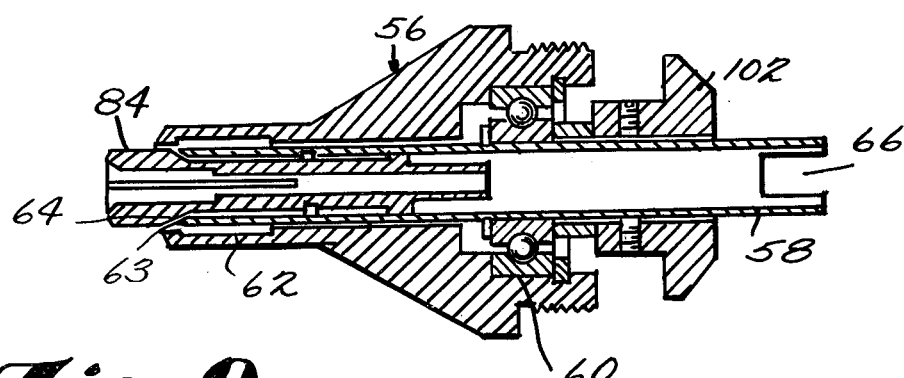
FIG. 6 is an enlarged cross sectional view of the nose collet assembly of the invention shown in FIG. 2.

The present invention as shown in FIGS. 1-21 concerns a specially designed wire and tip which is utilized in a unique surgical drill to provide an improved surgical instrument. In the invention the wire capsule assembly 20 shown in FIG. 16 is constructed in a wrap so that the capsule can be sterilized in ethylene oxide gas and the sterile capsule assembly 20 can be handled and installed in a chuck without contaminating the wire. The sterile capsule 20 is intended to be disposable so that a pre-sterilized encapsulated wire can be used in a non-sterile or sterile wire insertion machine without causing contamination of the wire. Once the wire has been used the remaining portion of the wire capsule is discarded. The wire which is used in the assembly preferably is formed with four flats formed as chords each subtending a center angle of 45° located in an equally spaced manner around the circumference. These flats 24 provide anti rotational keying with the chuck in the machine inserter. The tip of the wire 26 is designed to cut a hole in the bone smaller in diameter than the major diameter of the wire. This result is achieved by orienting a spade point construction approximately normal to the opposite flats 24 on the wire body 22. In this manner the length of the spade cutting tip 26 is restricted to about 92% of the major diameter of the wire 22. The spade point of the tip allows the wire to be more easily drilled into the bone. A small inner chuck 30 is mounted on the wire. The chuck 30 is constructed with internal flats 32 designed to prevent slippage of the chuck on the wire, and external flats 33 designed to prevent slippage of the chuck 30 within the machine chuck 42. A thin walled plastic or paper sleeve 34 encompasses the inner chuck and most of the wire length. A plastic or paper cap 40 encloses the wire tip extending in front of the inner chuck to keep it in a sterilized condition.

In use the encapsulated wire assembly 20 is inserted into a chuck 42 of the machine 50 used for wire insertion as is shown in FIG. 21. The chuck 42 of the insertion machine is tightened onto the inner chuck 30 of the capsule assembly through the plastic or paper sleeve 34. The inner chuck in turn grips the wire body 22 so that once it is installed in a tightened chuck of the machine, the cap 40 is removed exposing the tip of the sterile wire which is ready for use. The sterile cap 35 which goes over the end of the chuck can be constructed to protect further against contamination. While the cap and the sleeve or wall of the capsule assembly are preferably constructed of plastic it should be noted that paper can be substituted if such is desired. The wire itself is preferably constructed of stainless steel or other medically suitable non-toxic material which can be safely inserted into the bone structure or other parts of the body.

While the anti rotational features of the wire 22 and the inner chuck 30 are preferably flats, 24, 32 and 33, it should be noted that other anti rotational features such as teeth, grooves, or keys can be substituted if desired.

Figure 9:
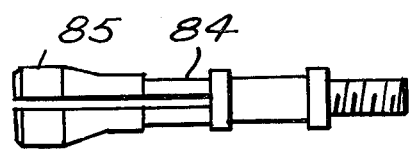
FIG. 9 is a side elevational view of the collet shown in FIG. 6.
Figure 7:
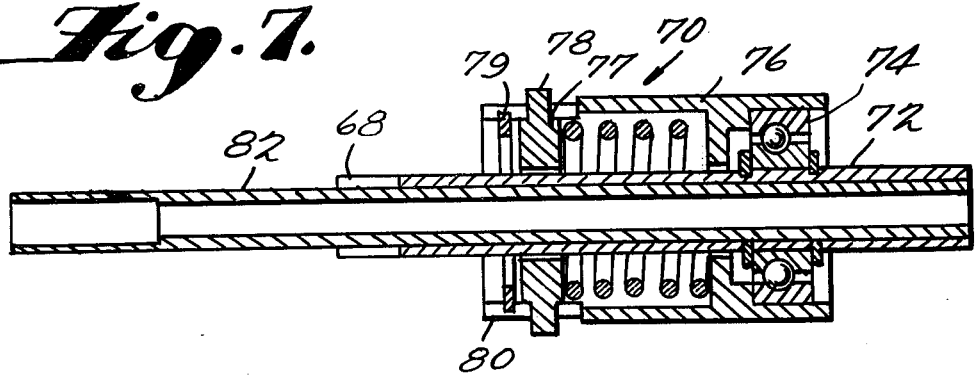
FIG. 7 is an enlarged cross section of the draw tube cartridge assembly of the invention.

The instrument 50 which operates and holds the prosthetic wires comprises an external casing 52 consisting of a handle housing 53, a wire drive housing 54 and a nose housing 56. A split collet 84 as shown in FIG. 9 is mounted in a collet tube 58 positioned in the nose housing 56 of the instrument and functions as the instrument chuck. The collet tube 58 is retained in a bearing assembly 60 which is mounted in the nose housing 56. The collet tube 58 is further supported by a nylon bushing 62. The front of the collet tube 58 is tapered inwardly forming an inner conical surface 63 to receive the conical shaped section 64 of the split collet member 84. The rear of the collet tube 66 is connected by a spline arrangement 68 to a draw tube assembly 70 as shown in FIG. 1. The draw tube assembly 70 comprises a draw tube 72 retained in a ball bearing assembly 74 which is in turn retained in a piston 76. A thrust ring 77 is free to move laterally in the piston and is limited in movement by the piston casing and a retaining ring 79 mounted in the piston casing. Pins 78 extend from the thrust ring and ride in grooves 80 to prevent rotation of the thrust ring. An inner draw tube 82 which is secured to the draw tube 72 extends forward inside the collet tube 58 to a point where it is attached to a split collet 84. The split collet 84 has an external conical section 64 which mates with the inner conical surface of the collet tube 58. Thus when the draw tube assembly 70 is moved in rearward direction, the conical portion 64 of the collet is pulled into the conical portion of the collet tube causing the jaws 85 of the split collet 84 to close.

An operating lever 94 mounted to one end of cam rod 88 extends downwardly alongside the instrument handle. The cam rod 88 extends across and through the drive housing. Two thrust bars 90 and 92 are located on either side of the piston 76 inside the drive housing and are provided with planar cutouts which bear against flats 89 formed on the cam rod 88 so that when the cam rod is rotated 90° by turning the lever 94 the thrust bars move rearwardly and apply pressure to pins 78 extending from the thrust ring 77. The pressure on the thrust ring is transmitted to the piston by means of a spring 98. When the operating lever 94 is rotated 90° the thrust bars cam against the pins, the thrust ring and spring to move the piston rearward. This movement moves the draw tube rearwardly causing the collet jaws to close which tightens the inner chuck 30 of the capsule assembly and grips the wire 22 as previously described. The holding force of the collet jaws is determined by the spring strength in the piston which limits the draw force and prevents overstressing of the instrument parts. Another spring 100 is located behind the piston and acts to return the piston and the draw tube assembly to its forward position when the lever 94 is returned to its original position. In this manner the grip of the collet jaws is released and the wire is free to slip in or out of the machine. Rotary motion is applied to the collet tube 58, draw tube 72 and split collet 84 through a bevel gear 102 secured to the collet tube 58. This gear is driven by a mating bevel gear 104 connected to a drive shaft 106 mounted on an electric motor 108. The electric motor 108 is solely housed within the instrument handle along with its power source. A trigger 110 mounted on the instrument handle acts through a cross bar 112 to activate and deactivate switch 114. The cross bar is structured to engage a flat 113 on the cam rod to prevent the switch 114 from operating when the split collet 84 is disengaged. Electric power is applied to the motor through the switch 114 from a power source comprising a rechargable battery pack 116 which is located in the handle. The battery pack 116 is held in place in the handle by a retaining cap 125 and a spring 120. Spring contacts 122 on the upper end of the battery pack 116 make contact with fixed electrical contacts 124 which are wired to the motor and the switch. The battery pack is keyed to a retaining cap 125 so that when the battery pack is rotated 180° by means of a retaining cap handle 118 the electrical contacts are reversed causing the motor to reverse direction. A key 126 on the inside of the handle engages a groove 128 around the retaining cap 125 thus holding the cap in place and providing a limit on its 180° rotation. When the retaining cap is pressed in, the key enters an exit groove which allows the retaining cap to rotate an additional 90° at which location the cap and battery pack can be removed so that the battery pack can be recharged or a new battery can be added to the instrument.

While the preferred embodiment of the invention has been disclosed, it is understood that the invention is not limited to such an embodiment since it may be otherwise embodied in the scope of the appended claims.

What is claimed is:

1. A wire adapted for use in a surgical environment comprising a uniform body, said body having a substantially circular cross section extending substantially along the full length of the wire being formed with four flats formed as chords so that said same cross section is broken up into alternate arcuate and planar sections, each flat subtending a center angle of 45 with said flats being located in an equally spaced manner around the circumference of the body and substantially extending along the full length of the body, one end of said wire defining a cutting tip forming a spade point, said spade point being oriented on the end of said wire and intersecting a pair of parallel flats on the wire and forming a cutting edge, the length of which is smaller than the length of a diagonal of the wire drawn from opposing arcuate sections.

2. A surgical wire for use in a surgical instrument adapted to insert the wire into a living bone material, said wire being left in the living bone material, said surgical wire comprising a body having a generally round cross section formed with a plurality of pairs of opposing flats in the form of chords extending substantially along its entire length to form a substantially uniform cross section of alternating curved surfaces and flat surfaces extending substantially along the entire length of the wire, said flats providing anti-rotational surfaces when said wire is inserted into a living bone material for a predetermined period of time allowing the bone cells to grow inward toward said flats, a spade cutting tip portion formed at one end of said wire, said spade tip portion being bounded by at least one pair of opposite positioned flats on the wire so that the diameter of a hole formed by the drilling of the spade cutting tip portion in the bone material when the wire is used as a drill bit is less than the length of a diagonal of the wire drawn from opposing curved surfaces.

3. A surgical wire adapted for use in a surgical environment, namely that of bone surgery, said surgical wire comprising a body, said body having a substantially circular cross section with four flats extending substantially the length of said wire and formed as chords, each flat subtending a center angle of about 45° with said flats being located in an equally spaced manner around the circumference of the body to define a uniform cross section of alternating curved and flat surfaces extending substantially along the entire length of the wire, one end of said wire defining a pointed tip, all of said flats providing anti-rotational surfaces which prevent rotation of said wire after it is imbedded in a living bone material.

4. A medically suitable nontoxic wire for use in a surgical instrument comprising a substantially cylindrical body with a uniform cross section extending substantially along its entire length, said cross section being formed with at least four flats forming chords substantially along its entire length with the uniform cross section of said body being generally circular and defining alternating arcuate and planar sections, said arcuate sections being formed with an outer surface having all points equidistant from the center axis of the wire, a spade cutting tip formed on one end of said wire body, and a pair of opposed flats defining the width of the spade cutting tip, the parallel flats on the wire body being positioned so that the diameter of a hole formed by drilling with the spade cutting tip while using the wire as a drill bit is about 92% of the length of a diagonal of the wire drawn from opposing arcuate sections.

* * * * *